United States Patent [19]
Klima

[11] Patent Number: 5,200,607
[45] Date of Patent: Apr. 6, 1993

[54] PHOTOELECTRIC SENSOR WITH DROPLET RESISTANT FACE

[75] Inventor: Catherine I. Klima, Freeport, Ill.

[73] Assignee: Honeywell Inc., Minneapolis, Minn.

[21] Appl. No.: 842,691

[22] Filed: Feb. 27, 1992

[51] Int. Cl.$^5$ .................................... H01J 5/16
[52] U.S. Cl. .................................... 250/216; 250/239
[58] Field of Search ............... 250/239, 216, 573, 577; 359/507

[56] References Cited

U.S. PATENT DOCUMENTS 4,792,699 12/1988 Duncan .................................. 250/577
5,115,129 5/1992 Johnson ................................. 250/239

Primary Examiner—David C. Nelms
Assistant Examiner—John R. Lee
Attorney, Agent, or Firm—William D. Lanyi

[57] ABSTRACT

A photodetector is provided with a housing that has a discontinuity formed in an outer surface of its light transmissive portion. The discontinuity serves to inhibit liquid droplets from adhering to the outer surface of the endface in the region where the discontinuity is located. Alternative embodiments of the present invention include discontinuities formed in the outer surfaces of housing windows which have flat inner surfaces or inner surfaces which are shaped to formed lenses. By preventing liquid droplets from adhering to the outer surface of the window, the present invention prevents the reflective liquid surfaces of droplets from creating false signals for the photodetector by reflecting light back from the light source toward a light sensitive component.

28 Claims, 7 Drawing Sheets

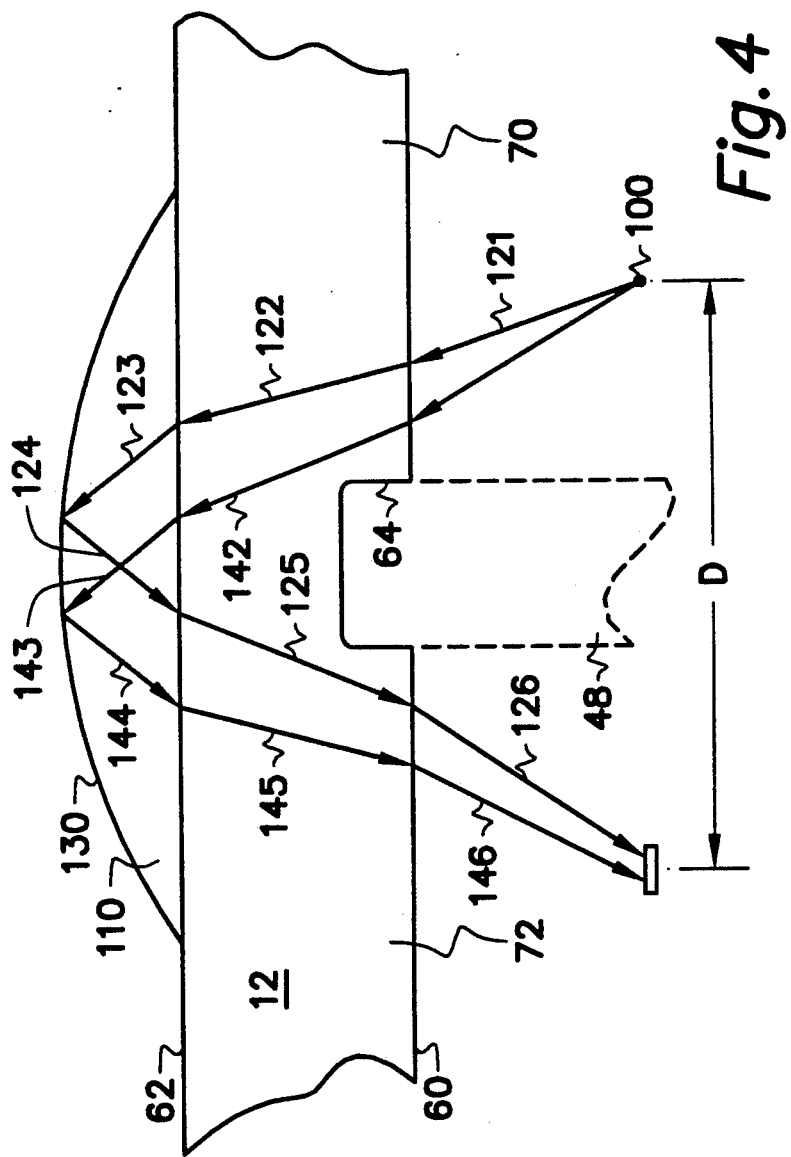

PHOTOELECTRIC SENSOR WITH DROPLET RESISTANT FACE

BACKGROUND OF THE INVENTION

1. Field of the Invention

The present invention relates generally to photoelectric sensors and, more particularly, to photoelectric sensors which provide a discontinuity in an outer surface of a transparent portion of the sensor to inhibit the formation of liquid droplets on the outer surface.

2. Description of the Prior Art

Photoelectric sensors are well known to those skilled in the art. Some photoelectric sensors comprise a housing structure which is shaped as a polyhedron while others are generally cylindrical. All photoelectric sensors provide some means for permitting light to pass through a portion of the housing toward a photosensitive device and some have a light transmissive member, or window, formed as an integral part of the sensor housing. U.S. patent application Ser. No. 07/662,864, which was filed on May 20, 1991 and is assigned to the assignee of the present application, describes a photoelectric device with a lens formed in its housing. However, it should be understood that many photoelectric sensors have housings made from several components that are attached together to form a housing structure and window. In addition, the window can be contained in any surface of the housing.

The formation of a light transmissive surface as an integral part of a sensor housing is one technique that has been employed to prevent moisture from leaking into the internal portion of the photoelectric device. By eliminating the normal seam between a lens and a housing structure that is necessary if the lens is not formed as an integral part of the housing structure, leakage through the seam is naturally eliminated. Many such steps have been taken in an attempt to waterproof the photoelectric sensor for use in harsh duty environments, particularly where the sensor must be periodically washed with a spray of liquid. Whether the end portion of the photoelectric sensor is merely light transmissive or formed into one or more lenses, the combination of the lens and the housing in a one piece structure improves the waterproof characteristic of the device.

When a photoelectric device is exposed to liquids, there exists the probability that the liquid will contact the smooth outer surface of its light transmissive portion, or window, and form droplets which can adhere to that smooth surface. When this occurs, a droplet can reflect light emanating from the photoelectric device back into the device to cause a false signal. This false signal can emulate the reflection of light from an object, as in a diffuse photoelectric application, or the reflection of light from a reflector, as in a retroreflective sensor application. In either case, the droplet of liquid on the face of the photoelectric sensor causes an erroneous signal and adversely affects the operation of the device. Although liquid droplets can adversely affect many different types of photoelectric sensors, this problem is severely exacerbated when the light transmissive portion of the housing structure is reduced in size to place the light source and photosensitive component close together. The possibility that a liquid droplet will be of sufficient size to adversely affect the sensor is increased when the light source and light detector are confined within a smaller space.

In view of the problem described above, it would be desirable to provide a photoelectric device that is not susceptible to false signals caused by droplets of liquid adhering to the outer surface of the light transmissive portion in a photoelectric sensor.

SUMMARY OF THE INVENTION

The present invention provides a discontinuity in the smooth outer surface of the window portion of a photoelectric sensor in order to prevent droplets of liquid from adhering to the outer surface of the housing in that region. In a preferred embodiment of the present invention, the sensor comprises a housing which has a light transmissive portion, or window. The light transmissive portion can be attached to other housing components or formed as an integral portion of a housing structure. In addition it can comprise flat surfaces or, alternatively, it can be formed in the shape of a lens. The light transmissive portion has a first segment and a second segment. In addition, the window of the photoelectric device has an inner surface and an outer surface and a discontinuity formed in the outer surface of the window. In a preferred embodiment of the present invention, the discontinuity is disposed between the first and second segments of the window and extends from one edge of the outer surface to a diametrically opposite edge of the outer surface.

One particularly preferred embodiment of the present invention comprises a housing which has an endface that is light transmissive and formed as an integral part of the housing. A light source is disposed within the housing and associated with a first portion of the endface to permit light from the light source to pass through the first portion in a direction from inside the housing to outside the housing. A light sensitive component is also disposed within the housing and associated with a second portion of the endface to permit light to pass through the second portion in a direction from outside the housing to inside the housing toward the light sensitive component. In a preferred embodiment of the present invention, the photoelectric sensor also comprises means for preventing light from passing directly from the light source to the light sensitive component within the housing.

Although a preferred embodiment of the present invention provides a discontinuity which is generally rectangular in cross sectional area and extends from one edge of the outer face to a diametrically opposite edge of the outer face, it should be understood that alternative cross sectional shapes are possible within the scope of the present invention and, in addition, that the discontinuity need not extend completely across the outer surface of the endface in all applications. Furthermore, the present invention can be used in association with housings that are polyhedrons or cylinders, with light transmissive portions that are plain or have lenses formed in them and in sensors that have detachable light transmissive portions or the type formed as an integral part of the housing.

BRIEF DESCRIPTION OF THE DRAWINGS

The present invention will be more fully understood from a reading of the Description of the Preferred Embodiment in conjunction with the drawing, in which:

FIG. 4 illustrates a problem that can occur with photodetector housings that have smooth flat outer surfaces;

DESCRIPTION OF THE PREFERRED EMBODIMENT

Figure 1:
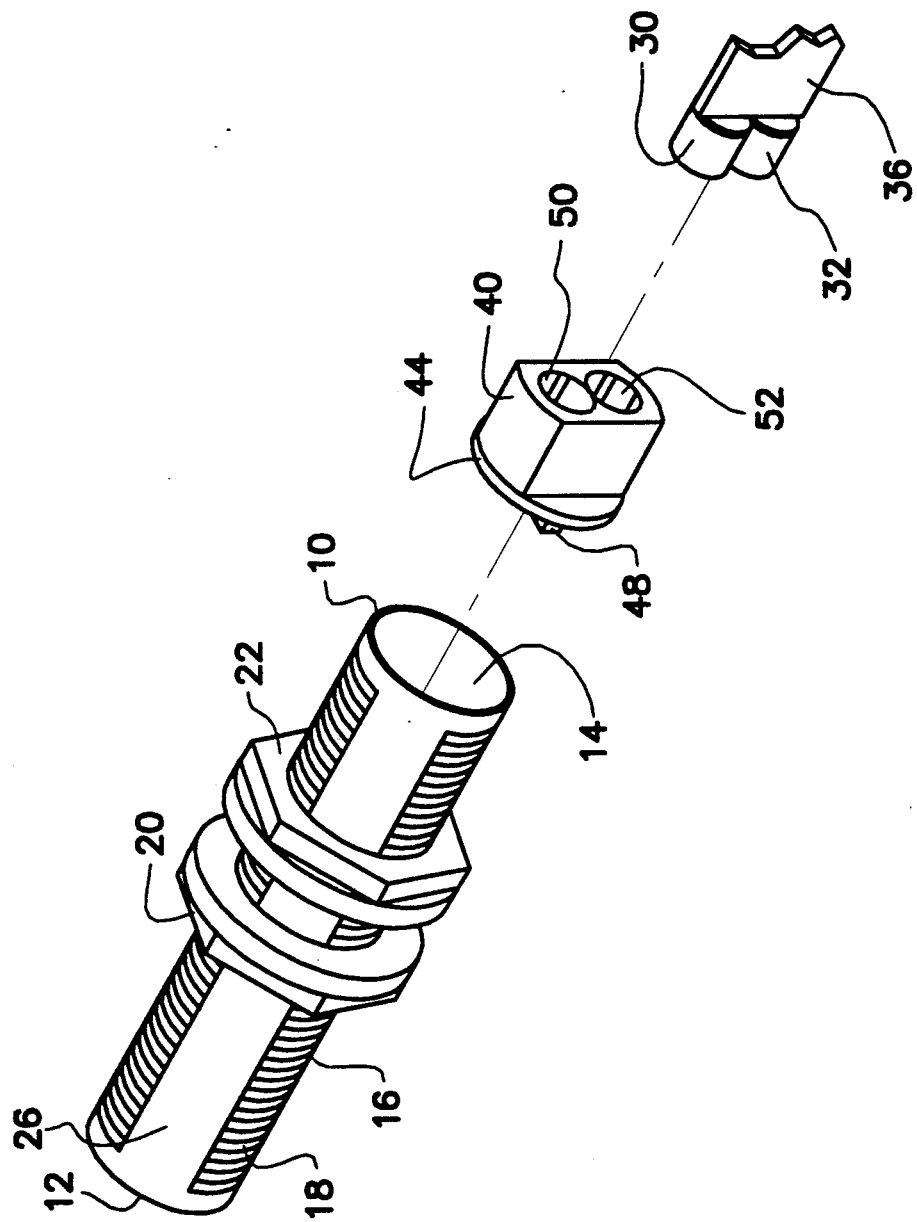
FIG. 1 illustrates a typical photodetector apparatus.

In the Description of the Preferred Embodiment, like components will be identified by like reference numerals.

FIG. 1 illustrates a photoelectric sensor that is known to those skilled in the art. The particular type of sensor shown in FIG. 1 comprises a cylindrical housing 10 that is formed with an integral endface 12 and an internal cavity 14 shaped to receive electronic components. The outer portion 16 of the housing is provided with threads 18 to permit one or more nuts, 20 and 22, to be arranged in threaded association with the threads 18. The nuts permit the photoelectric device to be attached to external objects. In certain types of cylindrical housings, a nonthreaded portion 26 is also provided on the outer surface.

In some photoelectric sensors, such as sensors used in diffuse or retroreflective applications, both a light source 30 and a light sensitive component 32 are included within the cavity 14 of the housing 10. In FIG. 1, the light source and the light sensitive component are shown mounted on a printed circuit board 36. A containment member 40 is provided to hold the light source and light sensitive component in their proper positions within the cavity 14. As shown in FIG. 1, the containment member 40 is provided with a cylindrical outer surface portion 44 which is shaped to be received in the inner cylindrical surface of the housing 10. In addition, a light barrier 48 is provided as a means for preventing light from passing directly from the light source 30 to the light sensitive component 32 within the cavity 14 without first passing through the endface 12 of the housing. The operation of the barrier 48 will be described in greater detail below. As can be seen in FIG. 1, the light source 30 and the light sensitive component 32 can be inserted into openings, 50 and 52, of the containment member.

The housing 10 shown in FIG. 1 can comprise an endface 12 of several different types. The particular style of light transmissive endface, or window, will depend on several factors. Some housings are provided with an endface window which has generally flat inner and outer surfaces with a depression formed in the inner surface to receive the barrier 48. Other housing endfaces are provided with lenses that are formed as part of the inner surface of the endface. In addition, some housings have the endface window formed as an integral part of the housing while other photoelectric devices utilize a lens that is attached to a housing member. Some housings are polyhedral in shape while others are cylindrical like the one shown in FIG. 1. Although it should be understood that the present invention is applicable in many different types of photoelectric devices, it will be described below in conjunction with generally cylindrical photoelectric housings which have an endface window formed as an integral part of the housing. The preferred embodiment of the present invention will be described in terms of both the endface window that comprises two generally flat surfaces on its inner and outer portions and in terms of an endface window which has two lenses formed in its inner surface.

Figure 2:
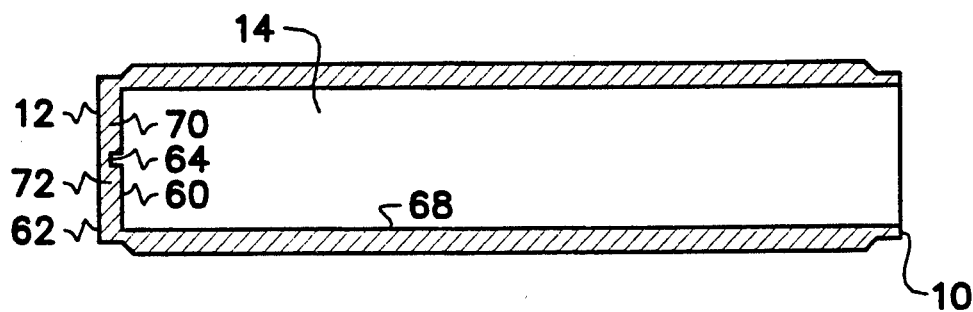
FIG. 2 is a sectional view of a photodetector housing having an endface with flat inner and outer surfaces.
Figure 3:
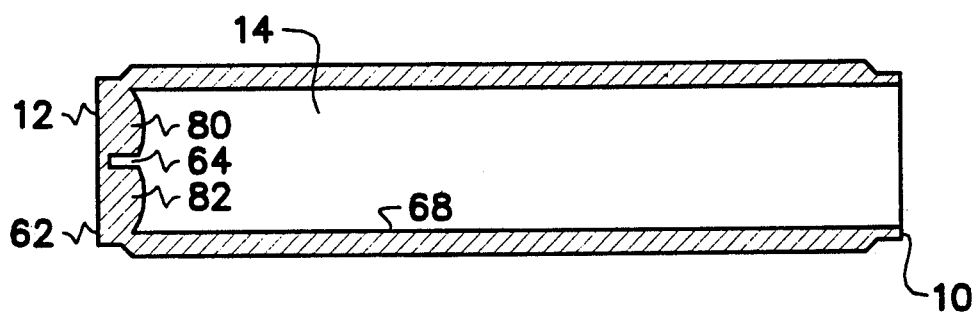
FIG. 3 is a sectional view of a photodetector housing with an endface shaped to form lenses in its inner surface.

FIGS. 2 and 3 show two typical versions of a cylindrical photoelectric detector housing 10. In FIG. 2, the window 12 has an inner surface 60 and an outer surface 62. Both the inner and outer surfaces of the window 12 are generally flat with the exception that the inner surface 60 is provided with a groove 64 that is shaped to receive the barrier 48. The cavity 14 contained within the cylindrical tube 68 is shaped to receive the electronic components as described above. When the containment member 40, shown in FIG. 1, is disposed within the inner cylindrical surface of the housing 10, the barrier 48 is disposed within the groove 64. This performs two useful functions. First, when the barrier 48 is aligned within the groove 64, the proper positioning of the light source 30 and light sensitive component 32 is assured. In addition, the barrier 48 prevents light from passing directly from the light source to the light sensitive component without first passing out of the housing 10 through the endface 12 and back again. The groove 64 divides the endface window into a first segment 70 and a second segment 72.

FIG. 3 shows another possible configuration of the housing 10. Endface 12 has a generally flat outer surface 62. The groove 64 on the inner surface of the endface 12 divides the endface into a first segment 80 and a second segment 82. In the embodiment shown in FIG. 3, the first and second endfaces, 80 and 82, are shaped to form lenses. These lenses focus the light as it passes from the light source and as it passes toward the light sensitive component.

With the possible exception of slightly different parameters relating to the circuit within the photodetector, the embodiments of the housing shown in FIGS. 2 and 3 are generally similar to each other. However, the shape of the inner surface of the endface is different in these two embodiments. The embodiment of FIG. 2 is generally flat while the embodiment in FIG. 3 is shaped to form lenses in its first and second segments. As described above, photoelectric devices which utilize generally flat outer surfaces on their windows sometimes experience a problem when the housings are subjected to a washdown with liquids. The liquids can form droplets on the outer flat surface 62 and the droplets can disadvantageously provide additional reflective surfaces that cause light from the light source 30 to be reflected back toward the light sensitive component 32 without being reflected by either a reflector in a retroreflective operational mode or an object to be sensed in the diffuse operational mode. FIG. 4 illustrates this problem in conjunction with a housing 10 such as that discussed above in association with FIG. 2.

In FIG. 4, the endface 12 is shown with its generally flat outer surface 62 and its generally flat inner surface 60. The groove 64 is shown extending into the inner surface 60 of the window to define a first segment 70 and a second segment 72. The light source 30 is represented as a single point light source and identified by reference numeral 100. The photosensitive component 32 is schematically represented by rectangle 104. The barrier 48 is shown in dashed line representation and is inserted into groove 64. The purpose of the barrier 48, as described above, is to prevent light from passing directly from light source 100 to the light sensitive component 104 without first passing through the endface 12. In normal operation of the photoelectric device, light is intended to pass from the light source 100, through the first segment 70 of the endface 12 and out of the housing. After being reflected by either an object to be sensed or a reflector, the light is expected to pass back toward the outer surface 62 of the endface 12, through the second segment 72 and toward the light sensitive component 104. However, as described above, applications which expose the housing 10 to liquids can result in a droplet 110 of liquid adhering to the outer surface 62 of the endface. When a droplet adheres to the window proximate the region between the first 70 and second 72 segments, a disadvantageous circumstance can result. That situation is schematically shown in FIG. 4. To illustrate the problem that can occur when a droplet 110 adheres to the outer surface of the endface, two light paths are shown. One light path comprises segments 121-126. The light which emanates from the light source 100 and passes along path 121 is slightly refracted at the inner surface 60 and continues to pass through the endface 12 along path 122. The light is again refracted at the outer surface 62 and continues along path 123. When the light strikes the surface 130 of the droplet 110, a portion of the light is reflected along light paths 124, 125 and 126 toward the light sensitive component 104. The surface 130 of the droplet 110 of liquid reflects a portion of the light to create a false signal at the photosensitive component 104. The light path identified by reference numerals 141-146 illustrates an alternative, but equally disadvantageous, light path from the light source 100 to the light sensitive component 104 which is caused by the surface 130 of the droplet of liquid proximate the region located between the first and second segments of the endface. It should be understood that light paths 121-126 and 141-146 are exemplary and that different paths would result for different indices of refraction of the droplet and the window were.

The problem illustrated in FIG. 4 is especially disadvantageous for smaller sensors which place the light source and photodetector much closer together than larger sensors, resulting is a smaller dimension D. The closer proximity of the light source and light sensor makes the device much more susceptible to the problems described above. A droplet which is too small to adversely affect a larger sensor could create significant problems for a smaller sensor with a reduced dimension D. The primary purpose of the present invention is to inhibit the adherence of droplets which are large enough to create the deleterious effect shown in FIG. 4.

Figure 5:
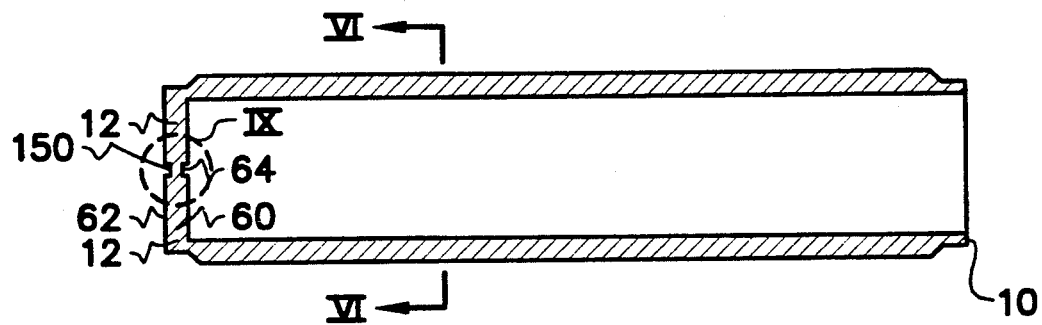
FIG. 5 is a sectional view of a housing made in accordance with the present invention.

In order to prevent a droplet larger than a predetermined size from adhering to the outer surface 62 of the endface 12 in the region between the first and second segments, the present invention provides a discontinuity which is formed in the outer surface 62. The discontinuity 150 is shown in FIG. 5. The housing 10 is the type which has an endface 12 that has a smooth outer surface 62 and a smooth inner surface 60 with a groove 64 formed in the inner surface 60 to receive the barrier 48.

The discontinuity 150 shown formed in the outer surface 62 prevents droplets of a sufficiently harmful size from adhering to the outer surface 62 in the region where the discontinuity is located. The operation of the present invention will be described in greater detail below in conjunction with FIG. 11.

Figure 6:
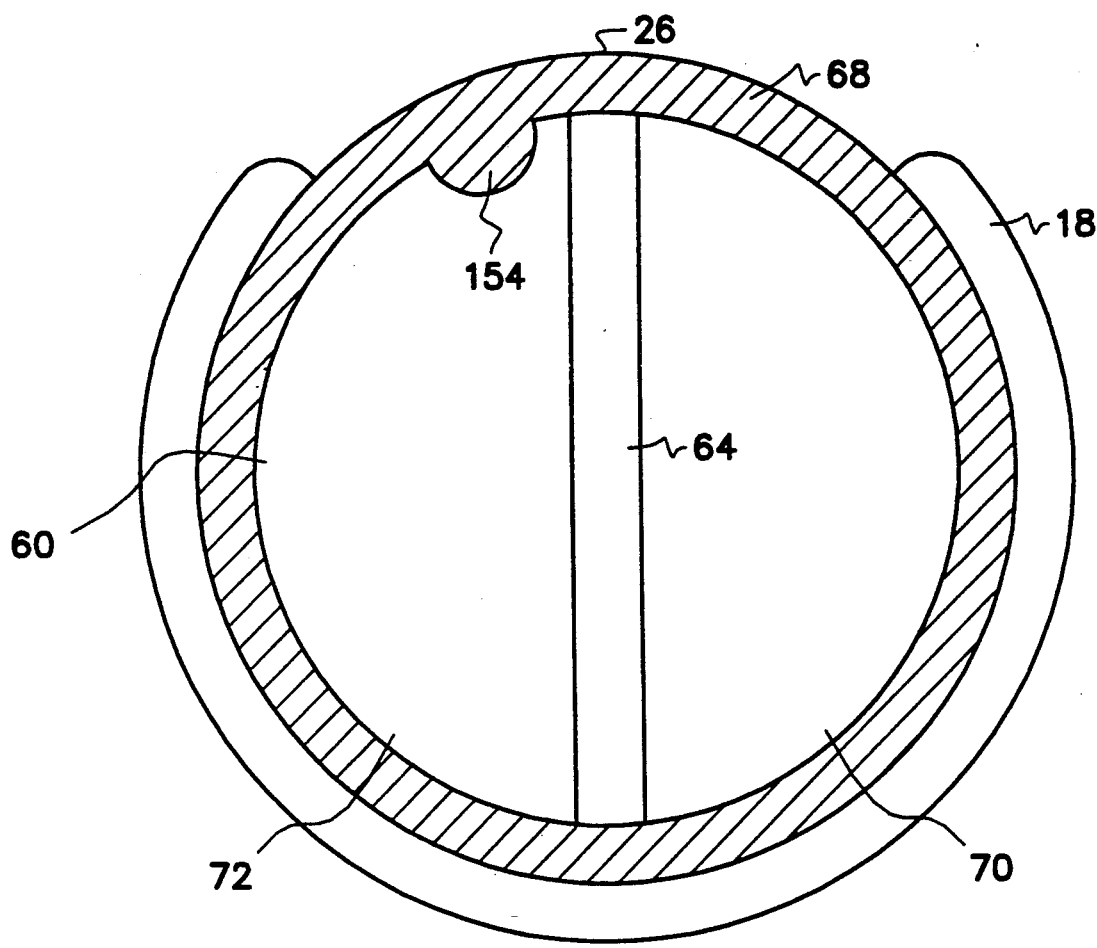
FIG. 6 is a sectional view of the housing shown in FIG. 5.

FIG. 6 is a sectional view of the housing shown in FIG. 5. In FIG. 6, the groove 64 that is formed in the inner surface 60 of the endface 12 divides the endface into first 70 and second 72 segments. Since FIG. 6 is a view of the internal side of the endface 12, the discontinuity 150 is not shown, but it should be understood that in a preferred embodiment of the present invention the discontinuity 150 is aligned with the groove 64 with the groove 64 being associated with the inner surface 60 and the discontinuity 150 being associated with the outer surface 62. The protrusion 154 is a locating device for the components disposed within the housing.

Figure 7:
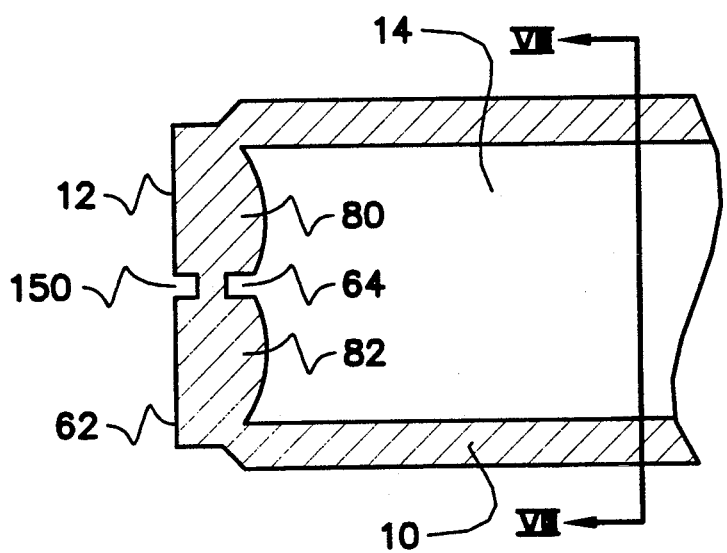
FIG. 7 is a sectional view of the present invention adapted for a housing with an endface shaped to form lenses in its inner surface.

FIG. 7 shows a sectional view of the front portion of a housing 10 which has an endface 12 that is shaped to form two lenses on the inner surface of the endface. The groove 64 is shown in the inner surface of the endface 12 dividing the endface into a first segment 80 and a second segment 82 which are both formed into individual lenses. The outer surface 62 is provided with a discontinuity 150 that is generally aligned with the groove 64, but on opposite surfaces of the endface.

Figure 8:
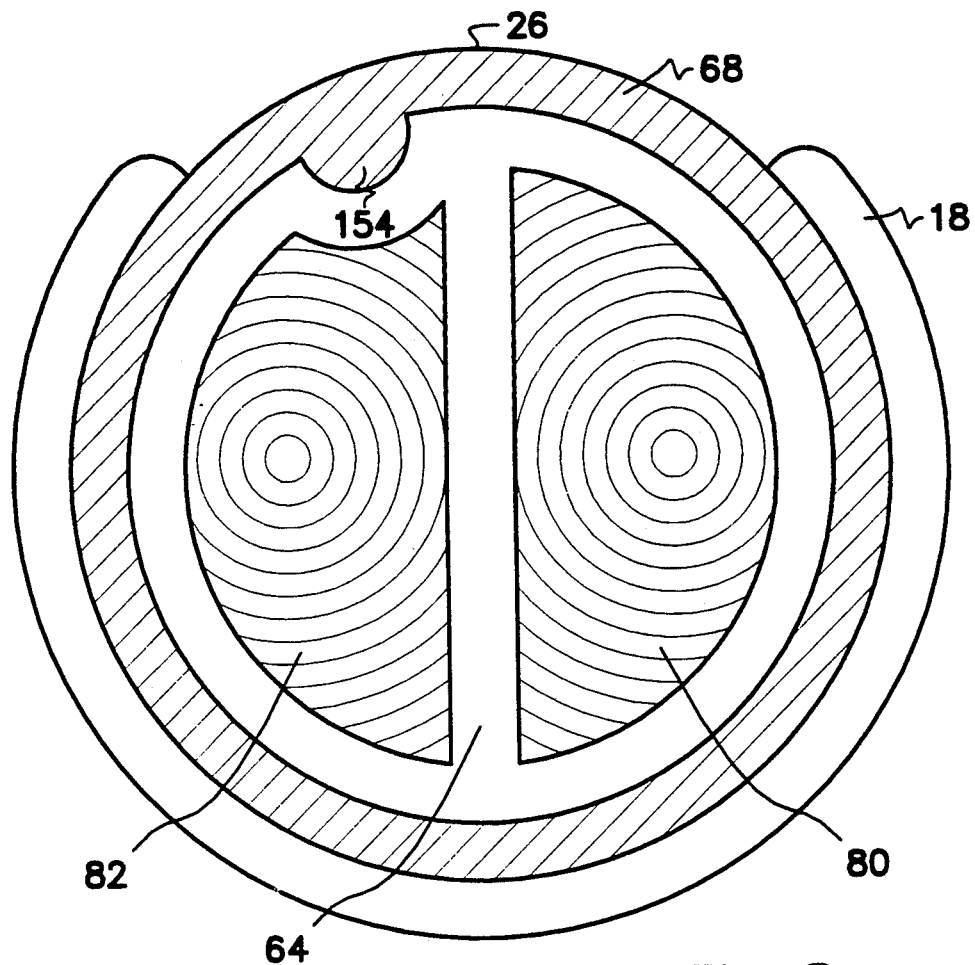
FIG. 8 is a sectional view of FIG. 7.

FIG. 8 is a sectional view of the housing shown in FIG. 7. As can be seen, the first segment 80 and the second segment 82 are shaped to form lenses in the endface 12. As discussed above in relation to FIGS. 4 and 5, the discontinuity 150 shown in FIG. 7 is aligned with the groove 64, but on the outer surface 62 of the endface 12, whereas groove 64 is formed in the inner surface of the endface 12.

Figure 9:
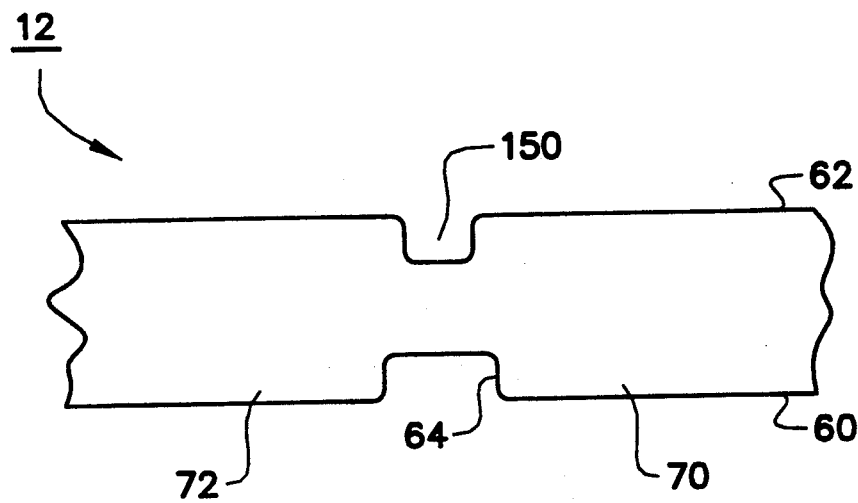
FIG. 9 is a detailed view of a portion of FIG. 5.

FIG. 9 shows an enlarged view of the portion of FIG. 4 contained within the dashed line circle. It shows a generally rectangular embodiment of the discontinuity 150 aligned with the groove 64. In one particular embodiment of the present invention, the groove 64 is approximately 0.045 inches wide and extends 0.020 inches into the inner surface 60. In that same particular embodiment of the present invention, the discontinuity 150 is generally rectangular in shape and approximately 0.030 inches wide and extends 0.020 inches into the outer surface 62 of the endface 12. The discontinuity 150 is disposed between the first 70 and second 72 segments of the endface. In addition, it is aligned with the groove 64 which, in turn, is shaped to receive the barrier 48 within it. Although a preferred embodiment of the present invention has been described and illustrated as having a discontinuity that is generally rectangular groove, it should be understood that alternative configurations of discontinuities can be used within the scope of the present invention.

Figure 10:
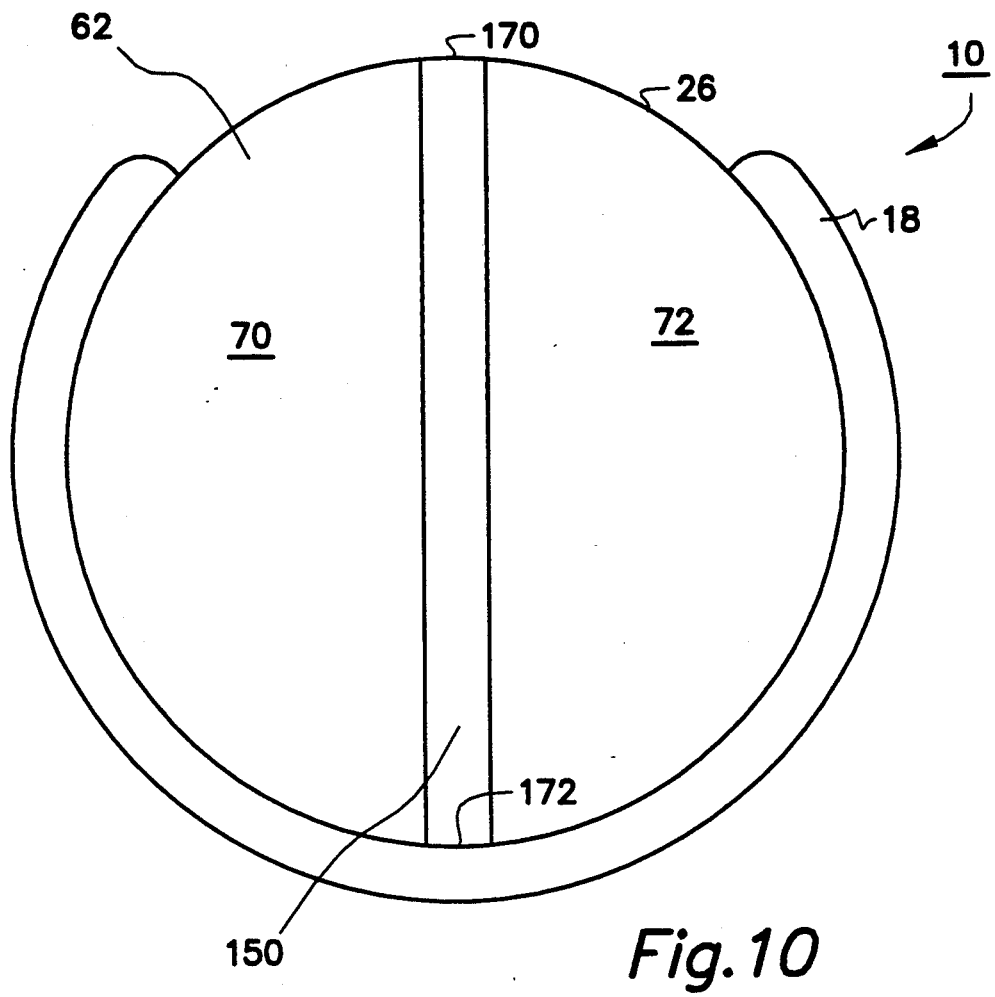
FIG. 10 is a end view of a housing with an endface having a discontinuity made in accordance with the present invention.

FIG. 10 shows an end view of a housing 10 with its outer surface 62 being divided into first 70 and second 72 segments. Between those segments, the discontinuity 150 extends from one edge 170 to a diametrically opposite edge 172 of the endface 12. In a preferred embodiment of the present invention, the discontinuity 150 extends completely across the endface along a diameter to bisect the window into the first and second segments. However, it should clearly be understood that alternative embodiments of the present invention may comprise discontinuities which do not extend completely across the window of the housing.

Figure 11:
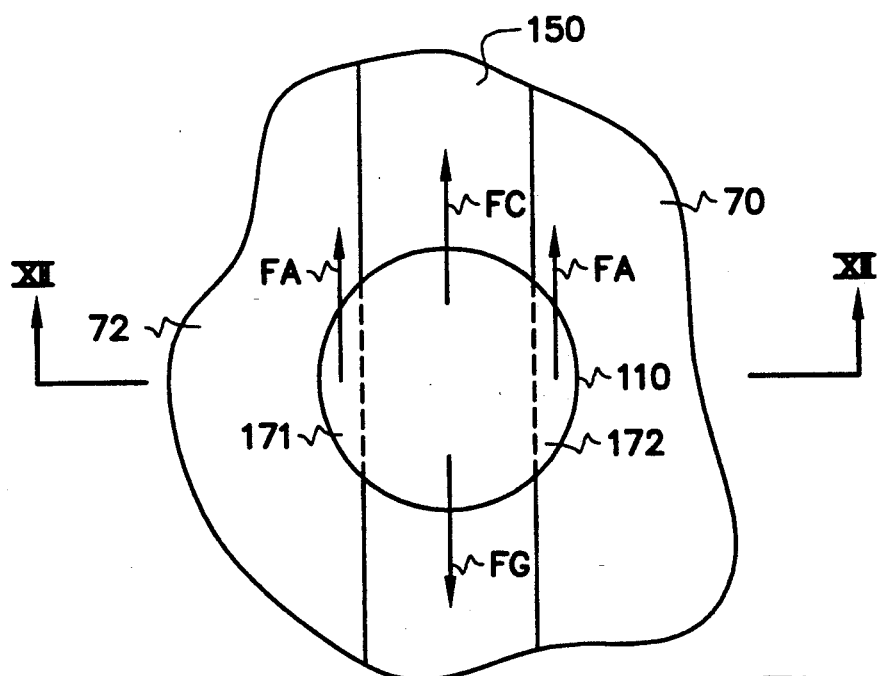
FIG. 11 is a schematic representation of the forces acting on a liquid droplet in relation to the present invention.
Figure 12:
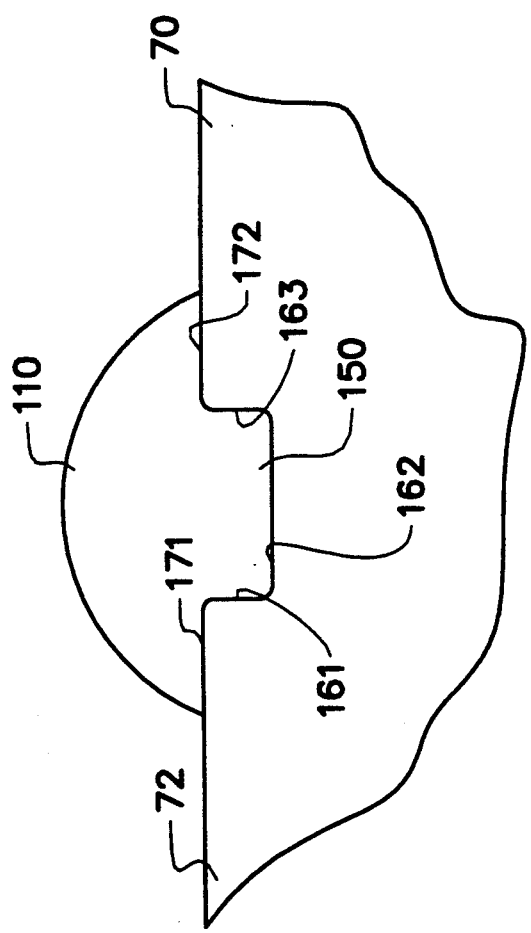
FIG. 12 is a side view of the illustration of FIG. 11.

FIGS. 11 and 12 illustrate the operation of the present invention. A droplet 110 is shown in a position within the region between segments 70 and 72 where it could cause the problems discussed above in conjunction with FIG. 4. It should be understood that FIGS. 11 and 12 represent the instant when the droplet 110 first comes into contact with the outside surface of the light transmissive portion of the sensor.

When the sensor is subjected to a spray of liquid, the surfaces 161, 162 and 163 of the discontinuity 150 cause the liquid to adhere to these surfaces and remain in the discontinuity. This is caused by the adhesive forces of the liquid and the capillary action within the groove. If a droplet 110 falls on the liquid filled discontinuity, as shown in FIGS. 11 and 12, a portion of the droplet is disposed over the liquid in the groove and other portions of the droplet are disposed in contact with the outer surface of the window, identified as areas 171 and 172. In the most common sensor position, with the outer surface of the window disposed in a vertical plane the droplet must rely on the adhesive forces FA at areas 171 and 172 and the cohesive force FC in the region over the liquid in the discontinuity 150 to overcome the force of gravity FG and maintain the droplet position in the disadvantageous position discussed above.

Because of the relatively small areas 171 and 172 and the relatively low cohesive characteristics of most fluids used to wash photoelectric sensors, the force of gravity FG overcomes these upward forces and causes the droplet to fall away from the outer surface of the light transmissive portion of the housing. Although FIG. 11 shows the discontinuity 150 in a vertical position, the same forces are experienced by the droplet when the discontinuity is horizontally positioned. The present invention creates the force imbalance described above by taking advantage of the relatively low cohesive force FC of most liquids and limiting the areas 171 and 172 where the adhesive forces FA can serve to maintain the droplet in a deleterious position between the two segments of the window. If the dimensions of the discontinuity is appropriately selected in relation to the characteristics of the liquid, the gravitational force FG on the droplet is sufficient to cause it to fall away from the central region of the window and thus prevent the disadvantageous situation that is illustrated in FIG. 4 and described above.

Although the present invention has been described with considerable detail and illustrated with significant specificity, it should be understood that alternative embodiments are within its scope. For example, although the discontinuity has been described as being a generally rectangular groove formed in the outer surface of the endface of a housing, alternative cross sectional shapes are possible. In addition, although the present invention has been described in relation to photodetector housings which are generally cylindrical and which have an endface formed as an integral part of the housing, these design options are not requirements of the present invention and do not limit its scope. Furthermore, the present invention can be used in photodetector housings whether they have lenses formed in their inner surfaces or have flat inner surfaces. In addition, the present invention is not limited by a particular type of light (e.g. visible light, infrared, etc.) and is not limited by a particular type of light sensitive component (e.g. phototransistor, photodiode, etc.). While a light emitting diode is used in a most particularly preferred embodiment of the present invention, it should be understood that alternative light sources are within its scope.

The embodiments of the invention in which an exclusive property or right is claimed are defined as follows:

1. A sensor, comprising:
   a housing;
   a light transmissive portion of said housing, said light transmissive portion having a first segment and a second segment, said light transmissive portion having an inner surface and a generally flat outer surface;
   a discontinuity formed in said outer surface of said light transmissive portion, said discontinuity being disposed between said first and second segments;
   a light source disposed within said housing and associated with said first segment to permit light from said light source to pass through said first segment in a direction from inside of said housing to outside of said housing;
   a light sensitive component disposed within said housing and associated with said second segment to permit light to pass through said second segment in a direction from outside of said housing to said light sensitive component; and
   means for preventing light from passing directly from said light source to said light sensitive component without passing through said light transmissive portion.

2. The sensor of claim 1, wherein:
   said first segment is shaped to form a first lens.

3. The sensor of claim 2, wherein:
   said second segment is shaped to form a second lens.

4. The sensor of claim 3, wherein:
   said light transmissive portion is an integral portion of said housing.

5. The sensor of claim 4, wherein:
   said housing is generally cylindrical.

6. The sensor of claim 5, wherein:
   said light source is a light emitting diode.

7. The sensor of claim 6, wherein:
   said light source is an infrared light emitting diode.

8. The sensor of claim 6, wherein:
   said light source is a visible light emitting diode.

9. The sensor of claim 6, wherein:
   said discontinuity is a groove formed in said outer surface.

10. The sensor of claim 6, wherein:
    said discontinuity extends from one edge of said outer surface to a diametrically opposite edge of said outer surface.

11. A sensor, comprising:
    a housing;
    a light transmissive portion of said housing, said light transmissive portion having a first segment and a second segment, said light transmissive portion having an inner surface and an outer surface; and
    a discontinuity formed in said outer surface of said light transmissive portion, said discontinuity being disposed between said first and second segments;
    a light source disposed within said housing and associated with said first segment to permit light from said light source to pass out of said housing through said first segment; and
    a light sensitive component disposed within said housing and associated with said second segment to permit light to pass into said housing through said second segment.

12. The sensor of claim 11, further comprising:
means for preventing light from passing directly from said light source to said light sensitive component without passing through said light transmissive portion.

13. The sensor of claim 11, wherein:
said first segment is shaped to form a first lens.

14. The sensor of claim 11, wherein:
said second segment is shaped to form a second lens.

15. The sensor of claim 11, wherein:
said light transmissive portion is an integral portion of said housing.

16. The sensor of claim 11, wherein:
said light source is a light emitting diode.

17. The sensor of claim 11, wherein:
said light source is an infrared light emitting diode.

18. The sensor of claim 11, wherein:
said light source is a visible light emitting diode.

19. The sensor of claim 11, wherein:
said discontinuity is a groove formed in said outer surface.

20. The sensor of claim 11, wherein:
said discontinuity extends from one edge of said outer surface to a diametrically opposite edge of said outer surface.

21. The sensor of claim 11, wherein:
said housing is cylindrical.

22. A photoelectric sensor, comprising:
a housing;
an window of said housing, said window having a first portion and a second portion, said window having an inner surface and an outer surface;
a light source disposed within said housing, said first portion being associated with said light source to permit light from said light source to pass through said first portion in a direction from inside of said housing to outside of said housing;
a light sensitive component disposed within said housing, said second portion being associated with said light sensitive component to permit light to pass through said second portion in a direction from outside of said housing to inside of said housing;
means for preventing light from passing directly from said light source to said light sensitive component within said housing; and
a discontinuity formed in said outer surface of said window, said discontinuity being disposed between said first and second portions.

23. The sensor of claim 22, wherein:
said first and second portions are each shaped to form a lens on said inner surface.

24. The sensor of claim 22, wherein:
said discontinuity extends across the entire diametric length of said outer surface.

25. The sensor of claim 22, wherein:
said light source is a light emitting diode.

26. The sensor of claim 25, wherein:
said light emitting diode in an infrared light emitting diode.

27. The sensor of claim 25, wherein:
said light emitting diode is a visible light emitting diode.

28. The sensor of claim 22, wherein:
said first and second portions are each generally semicircular and disposed in a side by side relationship.

* * * * *